US00PP24577P3

(12) United States Plant Patent
Coiner

(10) Patent No.: US PP24,577 P3
(45) Date of Patent: Jul. 1, 2014

(54) HYBRID TEA ROSE PLANT NAMED 'BIG GUY'

(50) Latin Name: *Rosa hybrida*
Varietal Denomination: Big Guy

(76) Inventor: James W. Coiner, Covina, CA (US)

( * ) Notice: Subject to any disclaimer, the term of this patent is extended or adjusted under 35 U.S.C. 154(b) by 90 days.

(21) Appl. No.: 13/573,190

(22) Filed: Aug. 29, 2012

(65) Prior Publication Data

US 2014/0068824 P1 Mar. 6, 2014

(51) Int. Cl.
*A01H 5/00* (2006.01)

(52) U.S. Cl.
USPC ..... Plt./134; Plt./101; Plt./130

(58) Field of Classification Search
USPC ..... Plt./101, 130, 134
See application file for complete search history.

*Primary Examiner* — Susan McCormick Ewoldt
(74) *Attorney, Agent, or Firm* — Christie, Parker & Hale, LLP

(57) ABSTRACT

A new variety of Hybrid Tea Rose suitable for garden decoration, having flowers of yellow coloration.

1 Drawing Sheet

Classification: The present invention relates to a new *Rosa hybrida* plant.

Variety denomination: The new plant has the varietal denomination 'BIG GUY'.

BACKGROUND OF THE INVENTION

This invention relates to a new and distinct variety of Hybrid Tea Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor is the following combination of characteristics: The plant has a compact upright growing growth habit, suitable for outdoor garden decoration.

Asexual reproduction of the new variety by budding as performed in Kern County Calif., shows that the foregoing and other distinguishing characteristics come true to form and are established and transmitted through succeeding asexual propagations. 'Big Guy' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Summer Sunshine' (U.S. Plant Pat. No. 2,078), by the following combination of characteristics: This is a unique cultivar of different color and foliage that is suitable for garden decoration.

BRIEF DESCRIPTION OF ILLUSTRATION

The accompanying photograph, FIG. 1, illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of two year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes usually bears its flowers singly, sometimes usually in clusters of two to five or more per stem. Flowers are borne in irregular rounded clusters on strong medium stems (about 37 cm to about 45 cm). Outdoors, the plant blooms abundantly and nearly continuously during the growing season. The flowers have a slight fruity fragrance.

BUD

The peduncle is about 4 cm to about 7 cm in length, of average caliper (about 2 cm to about 4 cm in diameter), and usually erect. It is usually smooth, with some stipitate glands, and few hairs. Peduncle color is near between 137c and 137d. Before the calyx breaks, the bud is about 1.3 cm to about 1.6 cm in diameter at the widest point, about 1.2 cm to about 2.6 cm in length, and pointed to ovoid in shape with a conspicuous neck. The surface of the bud bears some foliaceous appendages, stipitate glands and glandular bloom, usually with slender cut bristle-like foliaceous parts extending beyond the tip of the bud about one-fourth more of its length. Bud color is near between 12b and 12c.

The sepals are about 2.9 cm to about 3.6 cm in length and about 1 cm to about 1.6 cm in width at the widest point. The outer surface color of the sepal is near between 137c and 137d. The inner surface color of the sepal is near between 138b and 138c. Sepal margins are lined with some stipitate glands and hairs.

The receptacle of the flower is of moderately short to medium (about 1.3 cm to about 1.9 cm) and somewhat thin to average in caliper (about 1.3 cm to about 1.5 cm in diameter). The receptacle is somewhat pointed to ovoid in form. Its surface is moderately smooth with somewhat dry fleshy walls. The receptacle color is near between 137b and 137c.

As the petals open (after the calyx breaks), the bud is about 2 cm to about 2.9 cm in diameter at the widest point, about 3.3 cm to about 4 cm in length, and somewhat urn-shaped in form. The color of the under and upper surfaces of the newly opened petals is near between 12b and 12c. At the point where the petal attaches, there is a moderately small zone of near between 12a and 12b.

BLOOM

When fully open, the bloom ranges from about 8.5 cm to about 11 cm in diameter. Petalage is double with about 24 to 33 petals and about 2 to 3 petaloids irregularly arranged. When partially open, the bloom form is somewhat flat to cupped, and the petals are moderately loose to cupped to undulated with petal edges moderately rolled outward. When fully open, the bloom form is moderately flat to cupped to full and globular, and the petals are imbricated with petal edges somewhat rolled outward.

PETALS

The substance of the petals is very slightly leathery and crisp, and moderately medium to thick thickness, with upper surfaces somewhat satiny to velvety and under surfaces slightly satiny to velvety to matte. The petals are about 4.1 cm to about 6.1 cm in length and about 4 cm to about 6 cm in width at the widest point.

The outer petals are nearly round to oval to obovate in shape with apices very rounded to flat and sometimes slightly notched with one to two notches.

The inner petals are very moderately round to oval in shape with apices very rounded.

Petaloids are about 0.6 cm to about 1 cm in length and about 0.5 cm to about 0.9 cm in width at the widest point. Petaloids are shaped somewhat round to oval to ovate with rounded apices.

NEWLY OPENED FLOWER

The under and upper surface color of the outer petals is near between 12b and 12c.

The under and upper surface color of the intermediate petals is near between 12a and 12c.

The under and upper surface color of the inner petals is near between 12a and 12b.

The under and upper surface color of the petaloids are similar in coloration to the upper and under surfaces of the intermediate and inner petals.

The general tonality of the newly opened flower is near between 12b and 12c.

THREE-DAY OLD FLOWER

The under and upper surface color of the outer petals is near between 9c and 9d. At the point where the petal attaches, there is a moderately small zone of near between 12c and 12d.

The under and upper surface color of the inner petals is near between 12b and 12c.

The under and upper surface color of the petaloids are similar in coloration to the upper and under surfaces of the intermediate and inner petals.

The general tonality of the three-day-old flower is near between 12c and 12d.

On the spent bloom, the petals usually drop off cleanly except for persistent petaloids. In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 110) and are arranged regularly about the pistils; a few are mixed with petaloids or tucked in the calyx. The filaments are of very moderately long length (about 0.8 cm to about 1.8 cm) most with anthers. Filaments are near between 12a and 12b in color. The anthers are medium for the class and all open approximately at the same time. Anther color is near between 12a and 12c when immature and near between 13c and 17a at maturity. Pollen is moderate to abundant and near between 22a and 17b in color.

FEMALE REPRODUCTIVE ORGANS

Pistils vary in number (average about 85). The styles are somewhat uneven, long in length (about 0.6 cm to about 1.3 cm), average in caliper, and very somewhat loosely separated to bunched. Stigma color is near between 12b and 12c. Style color is near between 169a and 169d. Ovaries are usually enclosed in the calyx, although some may protrude from the calyx.

Hips have not been observed on this variety when grown in Wasco, Calif.

FOLIAGE

The compound leaves are usually comprised of three to five leaflets and are borne in normal quantities. The five-leaflet leaves are about 11.2 cm to about 15.7 cm in length, and about 10.5 cm to about 12.8 cm in width at the widest point, somewhat soft to leathery crisp in texture, and moderately semi-glossy to matte in finish. The terminal leaflets are about 4.5 cm to about 7.5 cm in length, and about 2.5 cm to about 4.7 cm in width at the widest point, shaped with moderately subacute apices and somewhat round bases. Their margins are serrate.

The upper surface color of the mature leaf is near between 137b and 137c. The under surface color of the mature leaf is near between 138a and 138b. The upper and under surface color of the young leaf is near between 138b and 138c.

The rachis is average in caliper and somewhat rough. The upper side is shallowly grooved with few hairs and stipitate glands on the edges of the grooves. The under side of the rachis is somewhat rough with few hairs and stipitate glands. The rachis color is near between 146b and 146c.

The stipules are about 1 cm. to about 1.4 cm in length and somewhat medium width to wide (about 1 cm to about 1.3 cm) with somewhat short to medium straight points that sometimes turn out at an angle of less than 45 degrees and recurve toward the stem. The stipules color is near between 146b and 146c.

The petiole is somewhat light to average in caliper and somewhat smooth. The upper side is deeply to moderately grooved. The under side of the rachis is moderately rough with some hairs and stipitate glands. The petiole color is near between 146b and 146c.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a compact upright medium height growth habit (about 105 cm to about 115 cm in height, and about 55 cm to about 42 cm spread at the widest point), with full branching. It displays vigorous growth and the canes are of medium to heavy caliper for the class.

The color of the major stems is near between 137b and 137d. They bear no prickles.

The color of the branches is near between 137c and 138c. They bear no prickles.

The color of the new shoots is near between 136b and 137d. They bear no prickles.

I claim:

1. A new and distinct Hybrid Tea Rose plant of the variety substantially as described and illustrated herein.

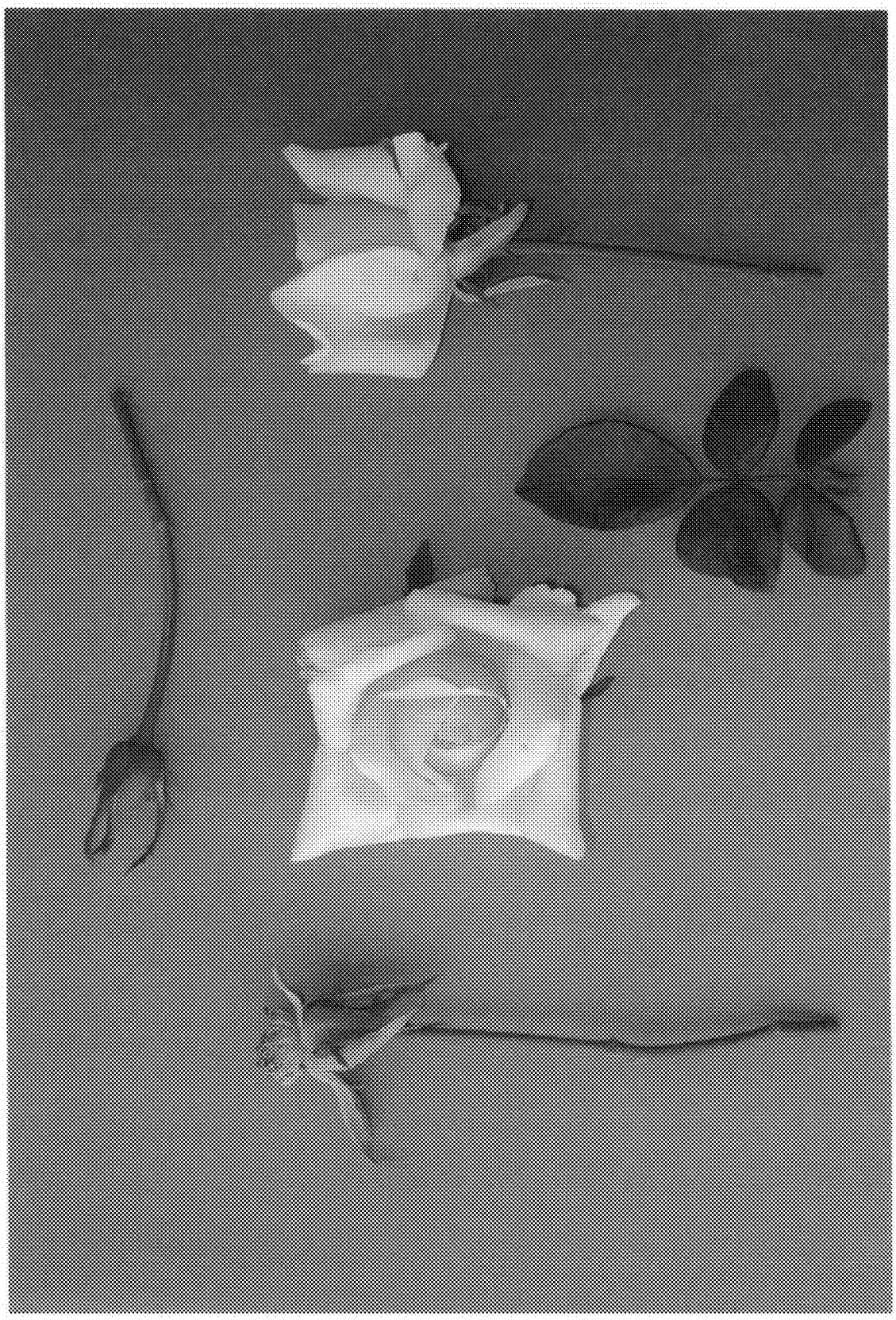

* * * * *